(12) United States Patent
Mandala et al.

(10) Patent No.: US 7,374,889 B2
(45) Date of Patent: May 20, 2008

(54) HUMAN SPHINGOSINE-1-PHOSPHATE PHOSPHATASE AND INHIBITION METHODS

(75) Inventors: Suzanne M. Mandala, Scotch Plains, NJ (US); Rosemary A. Thornton, Warren, NJ (US)

(73) Assignee: Merck & Co., Inc., Rahway, NJ (US)

( * ) Notice: Subject to any disclaimer, the term of this patent is extended or adjusted under 35 U.S.C. 154(b) by 78 days.

(21) Appl. No.: 10/467,219

(22) PCT Filed: Feb. 6, 2002

(86) PCT No.: PCT/US02/03833

§ 371 (c)(1),
(2), (4) Date: Aug. 6, 2003

(87) PCT Pub. No.: WO02/062134

PCT Pub. Date: Aug. 15, 2002

(65) Prior Publication Data

US 2004/0137447 A1 Jul. 15, 2004

Related U.S. Application Data

(60) Provisional application No. 60/267,000, filed on Feb. 7, 2001.

(51) Int. Cl.
*G01N 33/53* (2006.01)
(52) U.S. Cl. .................... 435/7.1; 435/6; 435/69.1; 435/7.1; 800/8; 530/350; 514/2; 514/12
(58) Field of Classification Search .................... 435/6, 435/69.1, 194, 7.1, 320.1, 252; 530/388, 530/350, 300; 536/23.2
See application file for complete search history.

(56) References Cited

U.S. PATENT DOCUMENTS 6,667,163 B2 * 12/2003 Mandala et al. ........... 435/70.1

OTHER PUBLICATIONS

Van Veldhoven, Direct Submission, Accession No. HSA293294, Sep. 7, 2000.*
Goetzl and An, "Diversity of cellular receptors and functions for the lysophospholipid growth factors lysophosphatidic acid and sphingosine 1-phosphate", FASEB J., vol. 12, pp. 1589-1598 (1998).
Spiegel, "Sphingosine 1-phosphate: a prototype of a new class of second messengers", Journal of Leukocyte Biology, vol. 65, pp. 341-344 (Mar. 1999).
Hisano et al., "Induction and Suppression of Endothelial Cell Apoptosis by Sphingolipids: A Possible in Vitro Model for Cell-Cell Interactions Between Platelets and Endothelial Cells", Blood, vol. 93, No. 12, pp. 4293-4299 (Jun. 15, 1999).
Wang, et al., "Sphingosine 1-Phosphate Stimulates Cell Migration through a Gi-coupled Cell Surface Receptor", The Journal of Biological Chemistry, vol. 274, No. 50, pp. 35343-35350 (Dec. 10, 1999).
Lee et al., "Vascular Endothelial Cell Adherens Junction Assembly and Morphogenesis Induced by Sphingosine-1-Phosphate", Cell, vol. 99, pp. 301-312 (Oct. 29, 1999).
Postma et al., "Sphingosine-1-phosphate rapidly induces Rho-dependent neurite retraction: action through a specific cell surface receptor", The EMBO Journal, vol. 15, No. 10, pp. 2388-2392 (1996).
Van Brocklyn et al., "Sphingosine 1-Phosphate-induced Cell Rounding and Neurite Retraction Are Mediated by the G Protein-coupled Receptor H218", The Journal of Biological Chemistry, vol. 274, No. 8, pp. 4626-4632 (Feb. 19, 1999).
van Koppen et al., "Activation of a High Affinity Gi Protein-coupled Plasma Membrane Receptor by Sphingosine-1-phosphate", The Journal of Biological Chemistry, vol. 271, No. 4, pp. 2082-2087 (Jan. 26, 1996).
Yamamura et al., "Sphingosine 1-Phosphate Regulates Melanoma Cell Motility through a Receptor-Coupled Extracellular Action and in a Pertussis Toxin-Insensitive Manner", Biochemistry, vol. 36, pp. 10751-10759 (1997).
Olivera et al., "Sphingosine-1-phosphate as second messenger in cell proliferation induced by PDGF and FCS mitogens", Nature, vol. 365, pp. 557-560 (Oct. 1993).
Choi, et al., "Calcium mobilization via sphingosine kinase in signalling by the FcεRI antigen receptor", Nature, vol. 380, pp. 634-636 (Apr. 1996).
Melendez et al., "FcγRI Coupling to Phospholipase D Initiates Sphingosine Kinase-mediated Calcium Mobilization and Vesicular Trafficking", The Journal of Biological Chemistry, vol. 273, No. 16, pp. 9393-9402 (Apr. 17, 1998.
Xia et al., "Tumor necrosis factor-α induces adhesion molecule expression through the sphingosine kinase pathway", Proc. Natl. Acad. Sci. USA, vol. 95, pp. 14196-14201 (Nov. 1998).
Kleuser et al., "1α,25-Dihydroxyvitamin D3 Inhibits Programmed Cell Death in HL-60 Cells by Activation of Sphingosine Kinase", Cancer Research, vol. 58, pp. 1817-1824 (May 1, 1998).

(Continued)

*Primary Examiner*—Hope Robinson
(74) *Attorney, Agent, or Firm*—Michael D. Yablonsky; Sheldon O. Heber

(57) ABSTRACT

The present invention provides polynucleotides and polypeptides of a human sphingosine-1-phosphate phosphatase, referred to herein as hSPP1. The polynucleotides and polypeptides are used to further provide expression vectors, host cells comprising the vectors, probes and primers, antibodies against the hSPP1 protein and polypeptides thereof, assays for the presence or expression of hSPP1 and assays for the identification of compounds that interact with hSPP1.

2 Claims, 2 Drawing Sheets

OTHER PUBLICATIONS

Meyer zu Heringdorf et al., "Sphingosine kinase-mediated Ca2+ signalling by G-protein-coupled receptors", The EMBO Journal, vol. 17, No. 10, pp. 2830-2837 (1998).

Mattie et al., "Sphingosine-1-phosphate, a Putative Second Messenger, Mobilizes Calcium from Internal Stores via an Inositol Trisphosphate-independent Pathway", The Journal of Biological Chemistry, vol. 269, No. 5, pp. 3181-3188 (1994).

Rani et al., "Divergence in Signal Transduction Pathways of Platelet-derived Growth Factor (PDGF) and Epidermal Growth Factor (EGF) Receptors", The Journal of Biological Chemistry, vol. 272, No. 16, pp. 10777-10783 (Apr. 18, 1997).

Van Brocklyn et al., "Dual Actions of Sphingosine-1-Phosphate: Extracellular through the Gi-coupled Receptor Edg-1 and Intracellular to Regulate Proliferation and Survival", The Journal of Cell Biology, vol. 142, No. 1, pp. 229-240 (Jul. 13, 1998).

Cuvillier et al., "Suppression of ceramide-mediated programmed cell death by sphingosine-1-phosphate", Nature, vol. 381, pp. 800-803 (Jun. 1996).

Perez et al., "Apoptosis-associated signaling pathways are required for chemotherapy-mediated female germ cell destruction", Nature Medicine, vol. 3, No. 11, pp. 1228-1232 (Nov. 1997).

Edsall et al., "Involvement of Sphingosine 1-Phosphate in Nerve Growth Factor-Mediated Neuronal Survival and Differentiation", The Journal of Neuroscience, vol. 17, No. 18, pp. 6952-6960 (Sep. 15, 1997).

Cuvillier et al., "Sphingosine 1-Phosphate Inhibits Activation of Caspases that Cleave Poly (ADP-ribose) Polymerase and Lamins during Fas- and Ceramide-mediated Apoptosis in Jurkat T Lymphocytes", The Journal of Biological Chemistry, vol. 273, No. 5, pp. 2910-2916 (Jan. 30, 1998).

Olivera et al., "Purification and Characterization of Rat Kidney Sphingosine Kinase", The Journal of Biological Chemistry, vol. 273, No. 20, pp. 12576-12583 (May 15, 1998).

Kohama et al., "Molecular Cloning and Functional Characterization of Murine Sphingosine Kinase", The Journal of Biological Chemistry, vol. 273, No. 37, pp. 23722-23728 (Sep. 11, 1998).

Nagiec et al., "The LCB4 (YOR171c) and LCB5 (YLR260w) Genes of Saccharomyces Encode Sphingoid Long Chain Base Kinases", The Journal of Biological Chemistry, vol. 273, No. 31, pp. 19437-19442 (Jul. 31, 1998).

Olivera et al., "Sphingosine Kinase Expression Increases Intracellular Sphingosine-1 phosphate and Promotes Cell Growth and Survival", The Journal of Cell Biology, vol. 147, No. 3, pp. 545-557 (Nov. 1, 1999).

Spiegel et al., "Sphingolipid metabolism and cell growth regulation", The FASEB Journal, vol. 10, pp. 1388-1397 (Oct. 1996).

Mandala et al., "Sphingoid base 1-phosphate phosphatase: A key regulator of sphingolipid metabolism and stress response", Proc. Natl. Acad. Sci. USA, vol. 95, pp. 150-155 (Jan. 1998).

Gottlieb et al., "The DPL1 Gene Is Involved in Mediating the Response to Nutrient Deprivation in Saccharomyces cerevisiae", Molecular Cell Biology Research Communications, vol. 1, pp. 66-71 (1999).

Mao et al., "The dihydrosphingosine-1-phosphate phosphatases of Saccharomyces cerevisiae are important regulators of cell proliferation and heat stress responses", Biochem. J., vol. 342, pp. 667-675 (1999).

Skrzypek et al., "Analysis of Phosphorylated Sphingolipid Long-Chain Bases Reveals Potential Roles in Heat Stress and Growth Control in Saccharomyces", Journal of Bacteriology, vol. 181, No. 4, pp. 1134-1140 (1999).

Saba et al., "The BST1 Gene of Saccharomyces cerevisiae Is the Sphingosine-1-phosphate Lyase", The Journal of Biological Chemistry, vol. 272, No. 42, pp. 26087-26090 (1997).

Mandala et al., "Sphingoid base 1-phosphate phosphatase: a key regulator of sphingolipid metabolism and stress response", Proc. Natl. Acad. Sci. USA, vol. 95, pp. 150-155 (Jan. 1998).

Mao et al., "Identification and Characterization of Saccharomyces cerevisiae Dihydrosphingosine-1-phosphate Phosphatase", The Journal of Biological Chemistry, vol. 272, No. 45, pp. 286090-28694 (Nov. 7, 1997).

Stukey et al., "Identification of a novel phosphatase sequence motif", Protein Science, vol. 6, pp. 469-472 (1997).

Toke et al., "Isolation and Characterization of the Saccharomyces cerevisiae LPP1 Gene Encoding a Mg2+independent Phosphatidate Phosphatase", The Journal of Biological Chemistry, vol. 273, No. 23, pp. 14331-14338 (Jun. 5, 1998).

Toke et al., "Isolation and Characterization of the Saccharomyces cerevisiae DPPI Gene Encoding Diacylglycerol Pyrophosphate Phosphatase", The Journal of Biological Chemistry, vol. 273, No. 6, pp. 3278-3284 (1998).

De Ceuster et al., "Identification and subcellular localization of sphinganine-phosphatases in rat liver", Biochem. J., vol. 311, pp. 139-146 (1995).

Brindley et al., "Mammalian Lipid Phosphate Phosphohydrolases", The Journal of Biological Chemistry, vol. 273, No. 38, pp. 24281-24284 (Sep. 18, 1998).

Carillo, H. and Lipton, D., "Th Multiple Sequence Alignment Problem in Biology", SIAM J. Applied Math, vol. 48, pp. 1073-1082 (1988).

Devereux et al., "A comprehensive set of sequence analysis programs for the VAX", Nucleic Acids Research, vol. 12, No. 1, pp. 387-395 (1984).

Altschul et al., "Basic Local Alignment Search Tool", J. Mol. Biol., vol. 215, pp. 403-410 (1990).

Evans et al., "Establishment in culture of pluripotential cells from mouse embryos", Nature, vol. 292, pp. 154-156 (Jul. 1981).

Bradley et al., "Formation of germ-line chimaeras from embryo-derived teratocarcinoma cell lines", Nature, vol. 309, pp. 255-256 (1984).

Gossler et al., "Transgenesis by means of blastocyst-derived embryonic stem cell lines", Proc. Natl. Acad. Sci. USA, vol. 83, pp. 9065-9069 (Dec. 1986).

Robertson et al., "Germ-line transmission of genes introduced into cultured pluripotential cells by retroviral vector", Nature, vol. 323, pp. 445-448 (Oct. 1986).

Jaenisch et al., "Transgenic Animals", Science, vol. 240, pp. 1468-1474 (Jun. 1988).

Jianhui and Saba, "Identification of the First Mammalian Sphingosine Phosphate Lyase Gene and Its Functional Expression in Yeast", Biochemical and Biophysical Research Communications, vol. 242, pp. 502-507 (1998).

Mandala et al., "Molecular cloning and characterization of a lipid phosphohydrolase that degrades sphingosine-1-phosphate and induces cell death", PNAS, vol. 97, No. 14, pp. 7859-7864 (Jul. 5, 2000).

Van Veldhoven and Mannaerts, "Sphinganine 1-phosphate metabolism in cultured skin fibroblasts: evidence for the existence of a sphingosine phosphatase", Biochem. J., vol. 299, pp. 597-601 (1994).

De Ceuster et al., "Identification and subcellular localization of sphinganine-phosphatases in rat liver", Biochem. J., vol. 311, pp. 139-146 (1995).

Stunff et al., "Characterization of Murine Sphingosine-1-phosphate Phosphohydrolase", The Journal of Biological Chemistry, vol. 277, No. 11, pp. 8920-8927 (Mar. 15, 2002).

Mandala, "Sphingosine-1-Phosphate Phosphatases", Prostaglandins & Other Lipid Mediators, vol. 64, pp. 143-156 (2001).

Mao et al., "Yeast Sphingosine-1-Phosphate Phosphatases: Assay, Expression, Deletion, Purification, and Cellular Localization by GFP Tagging", Methods in Enzymology, vol. 311, pp. 223-233 (1999).

Stunff et al., "Sphingosine-1-phosphate phosphohydrolase in regulation of sphingolipid metabolism and apoptosis", The Journal of Cell Biology, vol. 158, No. 6, pp. 1039-1049 (Sep. 16, 2002).

Stunff et al., Sphingosine-1-phosphate and lipid phosphohydrolases, Biochimica et Biophysica Acta 1582, pp. 8-17 (2002).

Ogawa et al., "Identification and Characterization of a Novel Human Sphingosine-1-phosphate Phosphohydrolase, hSPP2", The Journal of Biological Chemistry, vol. 278, No. 2, pp. 1268-1272 (Jan. 2003).

* cited by examiner

FIG. 1

```
CGGCCCGCCT TCCCGGGGGT TCCGTTATCA TGTCGCTGAG GCAGCGCCTG
GCCCAGCTGG TTGGCCGTCT GCAGGACCCG CAGAAAGTGG CCCGTTTCCA
GCGGCTGTGC GGGGTGGAAG CGCCGCCGCG CCGCTCAGCA GACCGGAGGG
AGGATGAGAA AGCGGAGGCG CCTCTCGCCG GAGACCCTCG ACTGCGAGGG
CGGCAGCCAG GGGCGCCTGG AGGCCCCAG CCTCCGGGA GCGACCGCAA
TCAGTGCCCG GCCAAGCCGG ACGGCGGCGG CGCCCCAAC GGCGTGCGGA
ACGGGCTGGC GGCCGAGCTG GGCCCGGCCT CGCCGCGGCG CGCGGGCGCT
CTGCGCCGCA ACTCGCTGAC GGGCGAGGAG GGCCAGCTGG CCCGCGTGAG
CAACTGGCCG CTCTACTGCC TGTTCTGCTT CGGCACGGAG CTGGGCAACG
AACTCTTCTA CATCCTGTTC TTCCCCTTCT GGATCTGGAA CCTGGACCCT
CTGGTGGGCC GGAGGCTCGT GGTCATCTGG GTGCTGGTCA TGTACCTGGG
CCAGTGCACC AAGGACATCA TCCGCTGGCC GAGGCCCGCC TCGCCGCCCG
TGGTCAAGTT GGAGGTCTTC TACAACTCTG AGTACAGCAT GCCCTCCACC
CATGCCATGT CCGGCACCGC CATCCCCATT TCTATGGTCC TCCTCACCTA
TGGCCGCTGG CAGTACCCTC TTATATATGG ACTGATTCTT ATTCCCTGCT
GGTGTTCTCT AGTTTGCCTA AGTAGAATTT ACATGGGAAT GCACTCTATT
CTGGATATTA TTGCTGGATT CCTATATACC ATTTTAATCT TAGCTGTCTT
CTATCCATTT GTGGACCTGA TTGACAACTT CAACCAAACT CACAAATATG
CTCCATTCAT CATCATCGGG CTTCATTTAG CTTTGGGGAT CTTTTCTTTC
ACTCTTGACA CCTGGAGCAC ATCCCGAGGA GACACAGCCG AGATACTAGG
AAGTGGTGCT GGAATTGCAT GTGGATCTCA TGTTACTTAT AACATGGGTC
TAGTATTAGA TCCTTCTCTA GATACATTAC CTTTAGCTGG GCCCCCATT
ACTGTGACTC TGTTTGGAAA AGCCATATTG CGGATCCTCA TAGGGATGGT
ATTTGTACTA ATAATCAGAG ATGTAATGAA AAAGATCACC ATTCCTTTAG
CCTGCAAAAT CTTCAATATA CCGTGTGATG ATATTCGAAA AGCAAGACAG
CACATGGAAG TTGAACTTCC TTATCGGTAT ATTACCTATG GAATGGTTGG
TTTCTCCATC ACATTTTTTG TTCCTTACAT ATTTTTCTTT ATTGGTATCT
CTTGATGGAG AAGTATTGTT TATGATAAGA AAGGAGGGTA TCAGTTACTG
ATACCCAAAA ATATATTCCA   (SEQ ID NO:1)
```

FIG. 2

MSLRQRLAQL VGRLQDPQKV ARFQRLCGVE APPRRSADRR EDEKAEAPLA GDPRLRGRQP
GAPGGPQPPG SDRNQCPAKP DGGGAPNGVR NGLAAELGPA SPRRAGALRR NSLTGEEGQL
ARVSNWPLYC LFCFGTELGN ELFYILFPF WIWNLDPLVG RRLVVIWVLV MYLGQCTKDI
IRWPRPASPP VVKLEVFYNS EYSMPSTHAM SGTAIPISMV LLTYGRWQYP LIYGLILIPC
WCSLVCLSRI YMGMHSILDI IAGFLYTILI LAVFYPFVDL IDNFNQTHKY APFIIGLHL
ALGIFSFTLD TWSTSRGDTA EIILGSGAGIA CGSHVTYNMG LVLDPSLDTL PLAGPPITVT
LFGKAILRIL IGMVFVLIIR DVMKKITIPL ACKIFNIPCD DIRKARQHME VELPYRYITY
GMVGFSITFF VPYIFFFIGI S* (SEQ ID NO:2)

HUMAN SPHINGOSINE-1-PHOSPHATE PHOSPHATASE AND INHIBITION METHODS

CROSS-REFERENCE TO RELATED APPLICATIONS

This application is a 371 of PCT/US02/03833 filed Feb. 6, 2002 which claims benefit to U.S. Provisional Application No. 60/267,000 filed on Feb. 7, 2001.

FIELD OF THE INVENTION

The invention relates to human sphingosine-1-phosphate phosphatase, polynucleotides encoding the enzyme and assays that measure the catabolism of sphingosine-1-phosphate by human sphingosine-1-phosphate phosphatase.

BACKGROUND OF THE INVENTION

Sphingosine-1-phosphate (SPP) is a bioactive sphingolipid metabolite which regulates diverse biological processes (reviewed in (Goetzl, et al., (1998) FASEB J.12, 1589-1598 and Spiegel, S. (1999) J. Leukoc. Biol. 65, 341-344.) Many of its actions are reported to be mediated by a family of specific cell surface G-protein coupled receptors (GPCR), known as EDG (endothelial differentiation genes) receptors. Binding of SPP to EDG-1 expressed on endothelial cells reportedly enhances survival (Hisano, et al., (1999) Blood 93, 4293-4299), chemotaxis and in vitro angiogenesis (Wang, et al., (1999) J. Biol. Chem. 274, 35343-35350) and adherens junction assembly leading to morphogenetic differentiation (Lee, et al., (1999) Cell 99, 301-312), whereas binding of SPP to EDG-5 and EDG-3 is reported to induce neurite retraction and soma rounding (Postma, et al., (1996) EMBO J. 15, 2388-2392 and Van Brocklyn, et al., (1999) J. Biol. Chem. 274, 46264632). Additional research indicates that SPP induces activation of $G_i$-gated inward rectifying K+-channels in atrial myocytes (van Koppen, et al., (1996) J. Biol. Chem. 271, 2082-2087) and inhibits motility of melanoma cells (Yamamura, et al., (1997) Biochemistry 36, 10751-10759) through as yet uncharacterized GPCRs.

SPP is also described as performing important roles inside cells. In response to diverse external stimuli, sphingosine kinase, the enzyme that catalyzes the phosphorylation of sphingosine to SPP, is activated (Olivera, et al., (1993) Nature 365, 557-560; Choi, et al., (1996) Nature 380, 634-636; Melendez, et al., (1998) J. Biol. Chem. 273, 9393-9402; Xia, et al., (1998) Proc. Natl. Acad. Sci. USA 95, 14196-14201; Kleuser, et al., (1998) Cancer Res. 58, 1817-1824 and Meyer zu Heringdorf, et al., (1998) EMBO J. 17, 2830-2837). Intracellular SPP in turn mobilizes calcium from internal stores independently of $InsP_3$ (Meyer zu Heringdorf, et al., (1998) EMBO J. 17, 2830-2837 and Mattie, et al., (1994) J. Biol. Chem. 269, 3181-3188), as well as eliciting diverse signaling pathways leading to proliferation (Rani, et al., (1997) J. Biol. Chem. 272, 10777-10783 and Van Brocklyn, et al., (1998) J. Cell Biol. 142, 229-240.) and suppression of apoptosis (Cuvillier, et al., (1996) Nature 381, 800-803; Perez, et al., (1997) Nature Med. 3, 1228-1232; Edsall, et al., (1997) J. Neurosci. 17, 6952-6960; Cuvillier, et al., (1998) J. Biol. Chem. 273, 2910-2916).

Because of its dual function as a ligand and second messenger and its pivotal role in cell growth and survival, the synthesis and degradation of SPP is expected to be tightly regulated in a spatial-temporal manner. Until recently, however, little was known of the enzymes involved in SPP metabolism. A previous report described the purification of sphingosine kinase to apparent homogeneity from rat kidney (Olivera, et al., (1998) J. Biol. Chem. 273, 12576-12583). Subsequently the first mammalian sphingosine kinase was cloned from rat and characterized (Kohama, et al., (1998) J. Biol. Chem. 273, 23722-23728). The kinase is described as belonging to a novel, highly conserved gene family (Kohama, et al., (1998) J. Biol. Chem. 273, 23722-23728 and Nagiec, et al., (1998) J. Biol. Chem. 273, 19437-19442). Enforced expression of the sphingosine kinase markedly enhanced the proliferation and survival of cells, substantiating the importance of intracellularly generated SPP in cell fate decisions (Olivera, et al., (1999) J. Cell Biol. 147, 545-548).

SPP can be metabolized by two distinct pathways. In one pathway, SPP is catabolized via a microsomal pyridoxal phosphate-dependent lyase to palmitaldehyde and phosphoethanolamine, which can then be utilized for the biosynthesis of glycerolipids. In a second pathway, SPP is dephosphorylated by specific phosphatases to sphingosine (Spiegel, et al., (1996) FASEB J. 10, 1388-1397).

Genetic manipulation studies in yeast have demonstrated an important role for long-chain phosphorylated sphingoid bases in growth and survival of yeast after nutrient deprivation and heat stress (Mandala, et al., (1998) Proc. Nat. Acad. Sci. USA 95, 150-155; Gottlieb, et al., (1999) Mol. Cell Biol. Res. Commun. 1, 66-71; Mao, et al., (1999) Biochem. J. 342, 667-675 and Skrzypek, et al., (1999) J. Bacteriol. 181, 1134-1140) in a manner which is reminiscent of their effects on mammalian cells. Recently, the yeast genes encoding the lyase and phosphatase enzymes of these two catabolic pathways were identified in S. cerevisiae (Saba, et al. (1997) J. Biol. Chem. 272, 26087-26090; Mandala, et al., (1998) Proc. Nat. Acad. Sci. USA 95, 150-155 and Mao, et al., (1997) J. Biol. Chem. 272, 28690-28694).

The yeast SPP phosphatases encoded by LBP1 and LBP2 are members of Type 2 lipid phosphate phosphohydrolases, a family of magnesium independent, membrane-bound enzymes that share sequence conservation within three domains that are predicted to be involved in the coordination and hydrolysis of the phosphate moiety (Stukey, et al., (1997) Protein Sci. 6, 469-472). A search of the yeast genome for enzymes containing the three conserved domains revealed the presence of 4 genes encoding putative Type 2 lipid phosphatases. Two of these, DPP1 and LPP1, were shown to encode phosphatases with activity against phosphatidic acid (PA), lysophosphatidic acid (LPA), and diacylglycerol pyrophosphate (DGPP) (Toke, et al., (1998) J. Biol. Chem. 273, 14331-14338 and Toke, et al., (1998) J. Biol. Chem. 273, 3278-3284). In contrast, LBP1 (also known as YSR2 or LCB3) and LBP2 (YSR3), encode phosphatases with remarkable specificity for phosphorylated sphingoid bases and without activity towards glycerolipid substrates (Mandala, et al., (1998) Proc. Nat. Acad. Sci. USA 95, 150-155; Mao, et al., (1997) J. Biol. Chem. 272, 28690-28694 and Skrzypek, et al., (1999) J. Bacteriol. 181, 1134-1140).

The presence of a high affinity SPP phosphatase activity with enzymatic properties similar to yeast SPP phosphatases has been described in crude rat liver and cerebellum extracts (De Ceuster, et al., (1995) Biochem. J. 311, 139-146). Although three isoforms of Type 2 lipid phosphate phosphohydrolases, known as LPP1/PAP2a, LPP3/PAP2b, and LPP2/PAP2c, have been cloned from mammalian cells (reviewed in (Brindley, et al., (1998) J. Biol. Chem. 273, 24281-24284)), these gene products appear to have broad substrate specificity with similar efficiencies against PA, LPA, SPP, ceramide-1-P, and DGPP, when assayed in vitro in lipid/detergent micelles.

SUMMARY OF THE INVENTION

The present invention provides polynucleotides encoding a human sphingosine-1-phosphate phosphatase(hSPP1), recombinant host cells containing hSPP1 polynucleotides, hSPP1 polypeptides, and methods of using the polynucleotides, polypeptides and host cells to conduct assays of sphingosine-1-phosphate phosphatase activity.

The polynucleotide and polypeptide of human SPP1, an enzyme involved in the catoblism of sphingosine-1-phosphate (SPP) are provided. The recombinant hSPP1 enzyme is catalytically active in the dephosphorylation of SPP. The enzyme is used in in vitro and whole cell assays to screen for compounds that alter the activity of the protein or interact with hSPP1 and, potentially, alter the expression of hSPP1. The invention includes the polynucleotide, protein encoded by the polynucleotide, host cells expressing the recombinant enzyme and extracts prepared from host cells expressing the recombinant enzyme, probes and primers, and the use of these molecules in assays.

An aspect of this invention is a polynucleotide having a sequence encoding a hSPP1 protein. In a particular embodiment the encoded protein has a sequence corresponding to SEQ ID NO:2. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucleotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has the sequence contained in sequence SEQ ID NO:1.

An aspect of this invention is a polynucleotide having a sequence of at least about 25 contiguous nucleotides that is specific for a naturally occurring polynucleotide encoding a hSPP1 protein. In particular preferred embodiments, the polynucleotides of this aspect are useful as probes for the specific detection of the presence of a polynucleotide encoding a hSPP1 protein. In other particular embodiments, the polynucleotides of this aspect are useful as primers for use in nucleic acid amplification based assays for the specific detection of the presence of a polynucleotide encoding a hSPP1 protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a hSPP1 protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in mammalian host cells. In other embodiments, the vector has regulatory regions appropriate for expression of the encoded protein in other eukaryotes, bacteria, yeasts, insect cells, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a hSPP1 protein, or a complementary sequence, and regulatory regions. In a particular embodiment the encoded protein has a sequence corresponding to SEQ ID NO:2. In preferred embodiments, the host cell is a eukaryote, yeast, insect cell, gram-positive bacterium, cyanobacterium or actinomycete. In a most preferred embodiment, the host cell is a mammalian cell.

An aspect of this invention is a process for expressing a hSPP1 protein in a host cell. In this aspect a host cell is transformed or transfected with an expression vector including a polynucleotide encoding a hSPP1 protein, or a complementary sequence. According to this aspect, the host cell is cultured under conditions conducive to the expression of the encoded hSPP1 protein. In particular embodiments the expression is inducible or constitutive. In a particular embodiment the encoded protein has a sequence corresponding to SEQ ID NO:2.

An aspect of this invention is a purified hSPP1 polypeptide having an amino acid sequence of SEQ ID NO:2 or the sequence of a naturally occurring mutant or polymorphic form of the protein.

An aspect of this invention is a method of determining whether a candidate compound can alter the activity of a hSPP1 polypeptide. According to this aspect a polynucleotide encoding the polypeptide is used to construct an expression vector appropriate for a particular host cell. The host cell is transformed or transfected with the expression vector and cultured under conditions conducive to the expression of the hSPP1 polypeptide. The cell is contacted with the candidate. Finally, one measures the activity of the hSPP1 polypeptide in the presence of the candidate. If the activity is lower relative to the activity of the protein in the absence of the candidate, then the candidate is a inhibitor of the hSPP1 polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO: 1. In particular embodiments, the relative activity of hSPP1 is determined by comparing the activity of the hSPP1 in a host cell. In some embodiments, the host cell is disrupted and the candidate is contacted to the released membrane extract. In other embodiments, the cells can be disrupted contacting with the candidate and before determining the activity of the hSPP1 protein. Finally, according to this aspect the relative activity can determined by comparison to a previously measured or expected activity value for the hSPP1 activity in the host under the conditions. However, in preferred embodiments, the relative activity is determined by measuring the activity of the hSPP1 in a control cell that was not contacted with a candidate compound. In particular embodiments, the host cell is a mammalian cell and the protein inhibited is the hSPP1 produced by the mammalian cell.

By "about" it is meant within 10% to 20% greater or lesser than particularly stated.

As used herein an "agonist" is a compound or molecule that interacts with and stimulates an activity of hSPP1.

As used herein an "antagonist" is a compound that interacts with hSPP1 and interferes with the interaction of hSPP1 and SPP.

As used herein an "inhibitor" is a compound that interacts with and inhibits or prevents hSPP1 from catalyzing the dephosphorylation of SPP.

As used herein a "modulator" is a compound that interacts with an aspect of cellular biochemistry to effect an increase or decrease in the amount of a polypeptide of hSPP1 present in, at the surface or in the periplasm of a cell, or in the surrounding serum or media. The change in amount of the hSPP1 polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

An aspect of this invention is a transgenic animal useful for the study of the tissue and temporal specific expression or activity of the hSPP1 gene in a non-human animal. The animal is also useful for studying the ability of a variety of compounds to act as agonists, antagonists or inhibitors of hSPP1 activity or expression in vivo or, by providing cells for culture or assays, in vitro. In an embodiment of this aspect of the invention, the animal is used in a method for the preparation of a further animal which lacks a functional endogenous hSPP1 gene. In another embodiment, the animal of this aspect is used in a method to prepare an animal which expresses a hSPP1 gene in the absence of the expression of a endogenous gene. In particular embodiments the non-human animal is a mouse. In further embodiments the hSPP1 gene is a wild-type hSPP1 gene or a mutant hSPP1 gene.

All of the references cited herein are incorporated by reference in their entirety as background material.

BRIEF DESCRIPTION OF THE DRAWINGS

FIG. 1 is the polynucleotide sequence of SEQ ID NO:1.
FIG. 2 is the polypeptide sequence of SEQ ID NO:2.

DETAILED DESCRIPTION OF THE INVENTION

The present invention provides a polynucleotide and polypeptide of a human sphingosine-1-phosphate phosphatase, referred to herein as hSPP1. The polynucleotide and polypeptide are used to further provide expression vectors, host cells comprising the vectors, probes and primers, antibodies against the hSPP1 protein and polypeptides thereof, assays for the presence or expression of hSPP1 and assays for the identification of compounds that interact with hSPP1.

Polynucleotides

Polynucleotides useful in the present invention include those described herein and those that one of skill in the art will be able to derive therefrom following the teachings of this specification. A preferred aspect of the present invention is a recombinant polynucleotide encoding a human SPP1 protein. One preferred embodiment is a nucleic acid having the sequence disclosed in FIG. 1, SEQ ID NO:1 and disclosed as follows:

```
cggcccgcct tcccgggggt tccgttatca tgtcgctgag gcagcgcctg (SEQ ID NO: 1)

gcccagctgg ttggccgtct gcaggacccg cagaaagtgg cccgtttcca gcggctgtgc ggggtggaag cgccgccgcg ccgctcagca gaccggaggg aggatgagaa agcggaggcg cctctcgccg gagaccctcg actgcgaggg cggcagccag gggcgcctgg aggcccccag cctcccggga gcgaccgcaa tcagtgcccg gccaagccgg acggcggcgg cgcccccaac ggcgtgcgga acgggctggc ggccgagctg ggcccggcct cgccgcggcg cgcgggcgct ctgcgccgca actcgctgac gggcgaggag ggccagctgg cccgcgtgag caactggccg ctctactgcc tgttctgctt cggcacggag ctgggcaacg aactcttcta catcctgttc ttccccttct ggatctggaa cctggaccct ctggtgggcc ggaggctcgt ggtcatctgg gtgctggtca tgtacctggg ccagtgcacc aaggacatca tccgctggcc gaggcccgcc tcgccgcccg tggtcaagtt ggaggtcttc tacaactctg agtacagcat gccctccacc catgccatgt ccggcaccgc catccccatt tctatggtcc tcctcaccta tggccgctgg cagtaccctc ttatatatgg actgattctt attccctgct ggtgttctct agtttgccta agtagaattt acatgggaat gcactctatt ctggatatta ttgctggatt cctatatacc attttaatct tagctgtctt ctatccattt gtggacctga ttgacaactt caaccaaact cacaaatatg ctccattcat catcatcggg cttcatttag ctttggggat cttttctttc actcttgaca cctggagcac atcccgagga gacacagccg agatactagg
```

-continued

```
aagtggtgct ggaattgcat gtggatctca tgttacttat aacatgggtc tagtattaga tccttctcta gatacattac ctttagctgg gcccccatt actgtgactc tgtttggaaa agccatattg cggatcctca tagggatggt atttgtacta ataatcagag atgtaatgaa aaagatcacc attcctttag cctgcaaaat cttcaatata ccgtgtgatg atattcgaaa agcaagacag cacatggaag ttgaacttcc ttatcggtat attacctatg gaatggttgg tttctccatc acatttttg ttccttacat attttctttt attggtatct cttgatggag aagtattgtt tatgataaga aaggagggta tcagttactg atacccaaaa atatattcca
```

The translation initiation and termination codons are underlined. A particularly preferred embodiment is a polynucleotide comprising the coding sequence of hSPP1 of SEQ ID NO:1.

The isolated nucleic acid molecules of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the hSPP1 gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the hSPP1 protein. Antisense strands are preferably less than full length strands having sequences unique or specific for RNA encoding the hSPP1 protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deaza-guanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000-100,000 fold. A chemically synthesized nucleic acid sequence is considered to be substantially purified when purified from its chemical precursors by the standards stated above.

The term "recombinant" is used to denote those polynucleotide preparations, constructs, expressions systems and cell lines containing the same which are made by the hand of man.

Included in the present invention are assays that employ further novel polynucleotides that hybridize to hSPP1 sequences under stringent conditions. By way of example, and not limitation, a procedure using conditions of high stringency is as follows: Prehybridization of filters containing DNA is carried out for 2 hr. to overnight at 65° C. in buffer composed of 6× SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and $5-20 \times 10^6$ cpm of $^{32}$P-labeled probe. Washing of filters is done at 37° C. for 1 hr in a solution containing 2× SSC, 0.1% SDS. This is followed by a wash in 0.1× SSC, 0.1% SDS at 50° C. for 45 min. before autoradiography.

Other procedures using conditions of high stringency would include either a hybridization step carried out in 5× SSC, 5× Denhardt's solution, 50% formamide at 42° C. for 12 to 48 hours or a washing step carried out in 0.2× SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, et al., 1989, Molecular Cloning: A Laboratory Manual, second edition, Cold Spring Harbor Laboratory Press. In addition to the foregoing, other conditions of high stringency which may be used are well known in the art.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (COMPUTATIONAL MOLECULAR BIOLOGY, Lesk, A. M., ed. Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds. Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073. Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCG program package (Devereux, J. et a., *Nucleic Acids Research* (1984)12(1):387), BLAST?, BLASTN, FASTA (Atschul, S. F. et al., *J Molec Biol* (1990)215:403).

As an illustration, by a polynucleotide having a nucleotide sequence having at least, for example, 95% "identity" to a reference nucleotide sequence of SEQ ID NO:1, it is intended that the nucleotide sequence of the polynucleotide is identical to the reference sequence except that the polynucleotide sequence may include up to five differences per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence.

Polypeptides

A preferred aspect of the present invention is a substantially purified form of the human SPP1 protein. A preferred embodiment is a protein that has the amino acid sequence which is shown in FIG. 2, in SEQ ID NO:2 and disclosed in single letter code as follows:

```
MSLRQRLAQL VGRLQDPQKV ARFQRLCGVE APPRRSADRR EDEKAEAPLA GDPRLRGRQP  (SEQ ID NO: 2)

GAPGGPQPPG SDRNQCPAKP DGGGAPNGVR NGLAAELGPA SPRRAGALRR NSLTGEEGQL

ARVSNWPLYC LFCFGTELGN ELFYILFFPF WIWNLDPLVG RRLVVIWVLV MYLGQCTKDI

IRWPRPASPP VVKLEVFYNS EYSMPSTHAM SGTAIPISMV LLTYGRWQYP LIYGLILIPC

WCSLVCLSRI YMGMHSILDI IAGFLYTILI LAVFYPFVDL IDNFNQTHKY APFIIGLHL
```

```
                                    -continued
ALGIFSFTLD TWSTSRGDTA EILGSGAGIA CGSHVTYNMG LVLDPSLDTL PLAGPPITVT

LFGKAILRIL IGMVFVLIIR DVMKKITIPL ACKIFNIPCD DIRKARQHME VELPYRYITY

GMVGFSITFF VPYIFFFIGI S*
```

The present invention also relates to biologically active fragments and mutant or polymorphic forms of the hSPP1 polypeptide sequence set forth as SEQ ID NO:2, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of hSPP1 function.

Using the disclosure of polynucleotide and polypeptide sequences provided herein to isolate polynucleotides encoding naturally occurring forms of hSPP1, one of skill in the art can determine whether such naturally occurring forms are mutant or polymorphic forms of hSPP1 by sequence comparison. One can further determine whether the encoded protein, or fragments of any hSPP1 protein, are biologically active by routine testing of the protein or fragment in a in vitro or in vivo assay for the biological activity of the hSPP1 protein. For example, one can express N-terminal or C-terminal truncations, or internal additions or deletions, in host cells and test for their ability to catalyze the dephosphorylation of sphingosine-1-phosphate.

It is known that there is a substantial amount of redundancy in the various codons which code for specific amino acids. Therefore, this invention is also directed to those DNA sequences that encode RNA comprising alternative codons which code for the eventual translation of the identical amino acid.

Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the catabolism of sphingosine-1-phosphate as compared to an unaltered hSPP1 protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type mSPP1 possesses a biological activity that is substantially similar to the biological activity of a wild type mSPP1. The term "functional derivative" is intended to include the "fragments," "mutants," "variants," "degenerate variants," "analogs," "orthologues," and "homologues" and "chemical derivatives" of a wild type mSPP1 protein that can catalyze the catabolism of sphingosine-1-phosphate.

The term "fragment" refers to any polypeptide subset of wild-type hSPP1. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the hSPP1. The term "variant" refers to a molecule substantially similar in structure and function to either the entire wild-type protein or to a fragment thereof. A molecule is "substantially similar" to a wild-type hSPP1-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length hSPP1 protein or to a biologically active fragment thereof.

As used herein in reference to a hSPP1 gene or encoded protein, a "polymorphic" hSPP1 is a hSPP1 that is naturally found in the population of animals at large. Typically, the genes for polymorphs of hSPP1 can be detected by high stringency hybridization using the hSPP1 gene as a probe. A polymorphic form of hSPP1 can be encoded by a nucleotide sequence different from the particular hSPP1 gene disclosed herein as SEQ ID NO:1. However, because of silent mutations, a polymorphic hSPP1 gene can encode the same or different amino acid sequence as that disclosed herein. Further, some polymorphic forms hSPP1 will exhibit biological characteristics that distinguish the form from wild-type hSPP1 activity, in which case the polymorphic form is also a mutant.

A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. It is most prefer proteins that have been purified to homogeneity, that is, at least 10,000-100,000 fold.

The term "recombinant" with respect to a polypeptide of the present invention refers only to polypeptides that are made by recombinant processes, expressed by recombinant cells or purified from natural cells as described above. Preparations having partially purified hSPP1 polypeptide are meant to be within the scope of the term "recombinant."

Expression of hSPP1

A variety of expression vectors can be used to express recombinant hSPP1 polypeptide in host cells. Expression vectors are defined herein as nucleic acid sequences that include regulatory sequences for the transcription of cloned DNA and the translation of their mRNAs in an appropriate host. Such vectors can be used to express genes in a variety of hosts such as yeast, bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that is involved in the binding of RNA polymerase to DNA and the initiation of RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant hSPP1 in bacterial cells. Commercially available bacterial expression vectors which are suitable for recombinant hSPP1 expression include, but are not limited to pQE (QIAGEN), pET11a or pET15b (NOVAGEN), lambda gt11 (INVITROGEN), and pKK223-3 (PHARMACIA).

Alternatively, one can express hSPP1 DNA in cell-free transcription-translation systems, or hSPP1 RNA in cell-free translation systems. Cell-free synthesis of hSPP1 polypeptide can be in batch or continuous formats known in the art.

One can also synthesize hSPP1 chemically, although this method is not preferred.

A variety of host cells can be employed with expression vectors to synthesize hSPP1 protein. These can include *E. coli*, Bacillus, and Salmonella. Insect and yeast cells can also be appropriate. However, the most preferred host cell is a mammalian host cell.

Following expression of hSPP1 in a host cell, hSPP1 polypeptides can be recovered. Several protein purification procedures are available and suitable for use. hSPP1 protein and polypeptides can be purified from cell lysates and extracts, or from culture medium, by various combinations of, or individual application of methods including detergent solubilization, ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The hSPP1 protein itself is useful in assays to identify compounds that alter the activity of the protein—including compounds that inhibit or stimulate the activity of the protein. The hSPP1 protein is also useful for the generation of antibodies against the protein, structural studies of the protein, and structure/function relationships of the protein.

Modulators, Agonist, Antagonists and Inhibitors of hSPP1

The present invention is also directed to methods for screening for compounds which modulate the expression of, stimulate or inhibit the activity of a hSPP1 protein. Compounds which modulate or inhibit hSPP1 can be DNA, RNA, peptides, proteins, or non-proteinaceous organic or inorganic compounds or other types of molecules. Compounds that modulate the expression of DNA or RNA encoding hSPP1 or are agonists, antagonists or inhibitors of the biological function of hSPP1 can be detected by a variety of assays. The assay can be a simple "yes/no" assay to determine whether there is a change in expression or activity. The assay can be made quantitative by comparing the expression or activity of a test sample with the level or degree of expression or activity in a standard sample, that is, a control. A compound that is a modulator can be detected by measuring the amount of the mRNA and/or hSPP1 produced in the presence of the compound. A compound that is an agonist, antagonist or inhibitor can be detected by measuring the specific activity of the hSPP1 protein in the presence and absence of the compound.

The proteins, DNA molecules, RNA molecules and antibodies lend themselves to the formulation of kits suitable for the detection and analysis of hSPP1. Such a kit would comprise a compartmentalized carrier suitable to hold in close confinement at least one container. The carrier would further comprise reagents such as recombinant hSPP1 or anti-hSPP1 antibodies suitable for detecting hSPP1. The carrier can also contain a means for detection such as labeled antigen or enzyme substrates or the like.

Assays

Assays of the present invention can be designed in many formats generally known in the art of screening compounds for biological activity or for binding to enzymes. Assays of the present invention can advantageously exploit the activity of hSPP1 in converting SPP to sphingosine or dihydrosphingosine-1-phosphate (DHSP) to dihydrosphingosine (DHS). For convenience, the description that follows will refer mostly to the conversion of SPP to sphingosine, however, either conversion can be followed in an assay.

The present invention includes methods of identifying compounds that specifically interact with hSPP1 polypeptides. Compounds that interact with the enzyme can stimulate or inhibit the activity of hSPP1. The specificity of binding of compounds having affinity for hSPP1 can be shown by measuring the affinity of the compounds to membranes from recombinant cells expressing a hSPP1 polypeptide. Expression of hSPP1 polypeptides and screening for compounds that bind to hSPP1 or that inhibit the conversion of SPP to sphingosine, provides an effective method for the rapid selection of compounds with affinity for hSPP1. The SPP can be radiolabeled but can also be labeled by other means known in the art and thereafter can be used to follow the conversion of the labeled SPP to sphingosine in assays of hSPP1 activity.

If one desires to produce a fragment of the hSPP1 or mutant, polymorphic or allelic variants of the hSPP1, one can test those products in the assays described below and compare the results to those obtained using an active hSPP1 polypeptide of SEQ ID NO:2. In this manner one can easily assess the ability of the fragment, mutant, polymorph or allelic variant to bind compounds, be activated by agonists or be inactivated or inhibited by antagonists of hSPP1.

Therefore, the present invention includes assays by which compounds that are hSPP1 agonists, antagonists, and inhibitors may be identified. The assay methods of the present invention differ from those described in the art because the present assays incorporate at least one step wherein the interaction of SPP and an hSPP1 polypeptide, preferably a recombinant polypeptide, is incorporated into the assay.

General methods for identifying ligands, agonists and antagonists are well known in the art and can be adapted to identify agonists and antagonists of hSPP1. The order of steps in any given method can be varied or performed concurrently as will be recognized by those of skill in the art of assays. The following is a sampling of the variety of formats that can be used to conduct an assay of the present invention.

Accordingly, the present invention includes a method for determining whether a candidate compound is an agonist or an inhibitor of hSPP1, the method of which comprises:

(a) transfecting cells with an expression vector encoding a hSPP1 polypeptide;

(b) allowing the transfected cells to grow for a time sufficient to allow hSPP1 to be expressed in the cells;

(c) exposing portions of the cells to labeled SPP in the presence and in the absence of the compound;

(d) measuring the conversion of the labeled SPP to sphingosine in the portions of cells; and (e) comparing the amount of conversion of SPP to sphingosine in the presence and the absence of the compound where a decrease in the amount of conversion of SPP to sphingosine in the presence of the compound indicates that the compound is an inhibitor of hSPP1 whereas an increase in the conversion of SPP to sphingosine indicates that the compound is an agonist of hSPP1.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. In this step the SPP and candidate compound can be applied to the cell sequentially or concurrently. It is preferred that the compound is applied first or that the compound and SPP are applied concurrently.

The above whole cell methods can be used in assays where one desires to assess whether a compound can traverse a cell membrane to interact with hSPP1. However, the above methods can be modified in that, rather than exposing the test cells to the candidate compound, membranes can be prepared from the cells and those membranes can be exposed to the compound. Such a modification utilizing membranes rather than cells is well known in the art and is described in, e.g., Hess et al., 1992. Particular methods of assaying membranes are described in the Examples below.

Accordingly, the present invention provides a method of using the interaction of SPP and hSPP1 for determining whether a candidate compound is an agonist or inhibitor of a hSPP1 polypeptide in membranes comprising:

(a) providing test cells by transfecting cells with an expression vector that directs the expression of hSPP1 in the cells;

(b) preparing membranes containing hSPP1 from the test cells;

(c) exposing the membranes to SPP under conditions such that the ligand binds to the polypeptide in the membranes;

(d) further exposing the membranes to a candidate compound under similar conditions;

(e) measuring the amount of conversion of SPP to sphingosine in the membranes in the presence and the absence of the compound;

(f) comparing the amount of conversion of SPP to sphingosine in the presence and the absence of the compound where a decrease in the amount of conversion of SPP to sphingosine in the presence of the compound indicates that the compound is an inhibitor of hSPP1; whereas an increase in the conversion of SPP to sphingosine indicates that the compound is an agonist of hSPP1.

As a further modification of the above-described methods, RNA encoding hSPP1 can be prepared as, e.g., by in vitro transcription using a plasmid containing hSPP1 under the control of a bacteriophage 17 promoter, and the RNA can be microinjected into Xenopus oocytes in order to cause the expression of hSPP1 in the oocytes. Compounds are then tested for binding to the hSPP1 or inhibition of activity of hSPP1 expressed in the oocytes. As in all assays of this invention, a step using the interaction of SPP and hSPP1 is incorporated into the assay.

Transgenic Animals

In reference to the transgenic animals of this invention, we refer to transgenes and genes. As used herein, a "transgene" is a genetic construct including a gene. The transgene is typically integrated into one or more chromosomes in the cells in an animal or its ancestor by methods known in the art. Once integrated, the transgene is carried in at least one place in the chromosomes of a transgenic animal. A gene is a nucleotide sequence that encodes a protein. The gene and/or transgene can also include genetic regulatory elements and/or structural elements known in the art.

The term "animal" is used herein to include all mammals, except humans. It also includes an individual animal in all stages of development, including embryonic and fetal stages. Preferably the animal is a rodent, and most preferably mouse or rat. A "transgenic animal" is an animal containing one or more cells bearing genetic information received, directly or indirectly, by deliberate genetic manipulation at a subcellular level, such as by microinjection or infection with recombinant virus. This introduced DNA molecule can be integrated within a chromosome, or it can be extra-chromosomally replicating DNA. Unless otherwise noted or understood from the context of the description of an animal, the term "transgenic animal" as used herein refers to a transgenic animal in which the genetic information was introduced into a germ line cell, thereby conferring the ability to transfer the information to offspring. If offspring in fact possess some or all of the genetic information, then they, too, are transgenic animals. The genetic information is typically provided in the form of a transgene carried by the transgenic animal.

The genetic information received by the non-human animal can be foreign to the species of animal to which the recipient belongs, or foreign only to the particular individual recipient. In the latter case, the information can be altered or it can be expressed differently than the native gene of the animal. Alternatively, the altered or introduced gene can cause the native gene to become non-functional.

As used herein, a "targeted gene" or "Knockout" (KO) transgene is a DNA sequence introduced into the germline of a non-human animal by way of human intervention, including but not limited to, the methods described herein. The targeted genes of the invention include nucleic acid sequences which are designed to specifically alter cognate endogenous alleles of the non-human animal.

An altered hSPP1 gene should not fully encode the same protein endogenous to the host animal, and its expression product can be altered to a minor or great degree, or absent altogether. In cases where it is useful to express a non-native hSPP1 protein in a transgenic animal in the absence of a endogenous hSPP1 protein we prefer that the altered hSPP1 gene induce a null, "knockout," phenotype for the native gene of the animal. However a more modestly modified hSPP1 gene can also be useful and is within the scope of the present invention.

A type of target cell for transgene introduction is the embryonic stem cell (ES). ES cells can be obtained from pre-implantation embryos cultured in vivo and fused with embryos (M. J. Evans et al., Nature 292:154-156(1981); Bradley et al., Nature 309:255-258 (1984); Gossler et al. Proc. Natl. Acad. Sci. USA 83:9065-9069 (1986); and Robertson et al., Nature 322:445-448 (1986)). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468-1474 (1988)). Animals are screened for those resulting in germline transformants. These are crossed to produce animals homozygous for the transgene.

Methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

This may have a therapeutic aim. The presence of a mutant, allele or variant sequence within cells of an organism, particularly when in place of a homologous endogenous sequence, may allow the organism to be used as a model in testing and/or studying the role of the hSPP1 gene or substances which modulate activity of the encoded polypeptide and/or promoter in vivo or are otherwise indicated to be of therapeutic potential.

EXAMPLE 1

Identification of Human Homologs to Mouse Sphingosine-1-Phosphate Phosphatases

To identify human homologs of the mouse sphingosine-1-phosphate (SPP) phosphatase encoded by mSPP1, the EST database was searched using the TBLASTN algorithm. Several human sequences in the EST database were identified with high homology to mSPP1 including gb:AA376229, gb:AA331563, gb:AA371461, gb:AA375349, gb:AA133909, gb:AA805328, and gsc:00005190.

Bacterial cultures transformed with these EST clones were obtained from ATCC or Merck Genome Sequencing Center and plasmid DNAs were prepared using WIZARD DNA Purification System (PROMEGA). DNA preparations were subjected to automated sequence analysis using the PRISM Dye Deoxy terminator cycle sequencing kit (APPLIED BIOSYSTEMS, Foster City, Calif.) on an ABI PRISM 377 instrument. T7 sequencing primer complementary to the vector was used in sequencing reactions. Database searches (GENBANK, EMBL, SWISS-PROTEIN, PIR, DEST) sequence alignments, and analysis of the nucleotide and protein sequences were carried out using TBLAST, the GCG Sequence Analysis Software Package (Madison, Wis.) and VectorNTI Contig Express. Sequence alignments confirmed the homology to mSPP1.

EXAMPLE 2

PCR Amplification of the hSPP1 3' end

A RACE (Rapid Amplification of cDNA Ends) methodology was initially employed to clone the human SPP phosphatase gene from cDNA libraries. Gene specific primers were designed based on the human ESTs AA376229, AA331563, AA371461, AA375349, AA133909 and AA805328. The gene specific primers had a 50-70% GC content and Tm≦70° C. Primers were paired with adapter primers and used to amplify the 5' and 3' ends using adapter ligated double stranded cDNAs and PCR kits purchased from CLONTECH (Marathon-Ready human placental cDNA, Marathon cDNA Amplification Kit, and Advantage PCR polymerase). An APPLIED BIOSYSTEMS GENE-AMP PCR 9700 instrument was used with cycling conditions of: 94° C. for 1 min; 5 cycles of 94° C. for 30 sec and 72° C. for 4 min; 5 cycles of 94° C. for 30 sec and 70° C. for 4 min; 30 cycles of 94° C. for 30 sec, 68° C. for 4 min; 70° C. for 7 min; and then hold at 4° C.

```
Primers
5'-CACCGCCATCCCCATTTCTATGG      (SEQ ID NO:3)
and

5'-GTGCTCCAGGTGTCAAGAGTGAAAG    (SEQ ID NO:4)
``` were used to amplify a 443 bp fragment from human fetal brain cDNA. The PCR product was isolated by GENECLEAN (BIO101) and ligated into pCR2.1 using a TA cloning kit (INVITROGEN) to make plasmid SPP(A)-pCR2.1.

```
Primers
5'-GGAAGTGGTGCTGGAATTGCATG      (SEQ ID NO:5)
and

5'-GCCTCCCATGTTCAACATCATGG      (SEQ ID NO:6)
``` were used to amplify a 930 base pair fragment from human placental cDNA. The PCR product was isolated by GENECLEAN (BIO101) and ligated into pCR2.1 to make plasmid SPP(B)-pCR2.1. The ligation reaction was transformed into DH5alpha competent cells (BRL), plated onto LB agar containing Ampicillin and incubated overnight at 37° C. Individual colonies were inoculated into 4 ml LB media containing Ampicillin, incubated overnight at 37° C., and plasmid DNA was isolated using WIZARD DNA Purification System (PROMEGA). The sequence of the PCR fragment within SPP(A)-pCR2.1 and SPP(B)-pCR2.1 included sequences identical to ESTs AA375349, AA376229 and AA133909 and contained the putative stop codon for the SPP phosphatase.

EXAMPLE 3

Construction of hSPP1 Clones for Expression

An 830 base pair BamHI-EcoRI fragment encoding the 3' end of the putative SPP phosphatase was isolated from the SPP(B)-pCR2.1. A 1222 base pair SalI-BamHI fragment encoding the 5' end of the SPP phosphatase was isolated directly from gsc:00005190 DNA (amyg2_p0b09 in pBluescript II SK-). The two restriction fragments were purified with GENECLEAN and ligated into E.Coli cloning vector pGEM-3Zf(+) at its SalI and EcoRI sites to give the complete SPP phosphatase coding sequence(SPP-pGEM3). A 2.3 Kb HincII-EcoRI fragment containing the complete coding region was isolated from SPP-pGEM3 and cloned into the mammalian expression vector pcDNA3.1zeo(−) (INVITROGEN) at its EcoRV and EcoRI sites to make plasmid hSPP1-pcDNA3.1. Ligation reactions were transformed into DH5alpha competent cells (BRL), plated onto LB agar containing Ampicillin and incubated overnight at 37° C. Individual colonies were inoculated into 4 ml LB media containing Ampicillin, incubated overnight at 37° C., and plasmid DNA was isolated using WIZARD DNA Purification System (PROMEGA). The nucleotide sequences of the intact hSPP1 was determined by automated sequencing.

EXAMPLE 4

Expression of Phosphatase Activity in Mammalian Cells

Transfection-quality DNA was prepared for plasmid hSPP1-pcDNA3.1 using endotoxin-free QIAGEN Maxi protocol (QIAGEN, Chatsworth, Calif.). Human embryonic kidney (HEK293) cells were maintained in high glucose Dulbecco's modified Eagle's medium (DMEM) containing 100 U/ml penicillin, 100 µg/ml streptomycin and 2 mM L-glutamine supplemented with 10% fetal bovine serum. Cells ($1\times10_6$) were transfected with 20 µg of plasmid DNA by the $CaCl_2$ procedure using a kit from SPECIALTY MEDIA (Lavallette, N.J.). Cells were harvested 48 hours after transfection with enzyme-free dissociation solution (SPECLALTY MEDIA, Lavallette, N.J.). The cells were washed 3 times in cold PBS and then lysed in hypotonic buffer consisting of 1 mM TrisCl pH 7.2 and a protease inhibitor cocktail for 10 min at 4° C. Cell debris was removed by centrifugation at 1,000× g for 5 min at 4° C., and the supernatant fluid was recentrifuged at 40,000× g for 30 min. The pellet was suspended at a protein concentration of approximately 2 mg/ml in 40 mM Tris/Cl pH 7.5, protease inhibitor cocktail, and 20% glycerol. Dihydrosphingosine-1-phosphate phosphohydrolase activity was measured in 200□1 containing 50 mM $KPO_4$ pH 7.2, 0.02% tergitol (NP-40), 0.076% BSA, 2□M [$^3$H]dihydrosphingosine-1-phosphate (40,000 cpm), 2 mM semicarbazide, and 0.3 to 5 µg of membrane protein. Following a 40 min incubation at 37° C., the assay was terminated with 200 µl 7 M NH4OH. One ml of chloroform:methanol (3:2) was added and 50 µl of the chloroform layer was counted by liquid scintillation.

Expression of hSPP1 in HEK293 resulted in a 3 to 5 fold increase in dihydrosphingosine-1-phosphate phosphohydrolase activity compared to vector transfected cells.

EXAMPLE 5 mRNA Expression of mSPP1 in Mammalian Tissues

Human brain, cancer and multiple tissue Poly(A)+RNA blots (CLONTECH) containing 2 µg of RNA per lane were probed with a 550 bp EcoRI fragment from SPP(A)-pCR2.1 that was gel purified and labeled with $^{32}$P-dCTP by random priming. Blots were hybridized in EXPRESSHYB Solution (CLONTECH) at 68° C. for 1 h and washed following the manufacturer's protocol. Bands were quantified using a MOLECULAR DYNAMICS STORM 860 and normalized to the amount of actin message present.

A single 3.8 kb transcript was detected in 22 of 23 human tissues that were surveyed indicating that this gene is ubiquitously expressed in humans.

EXAMPLE 6

Inhibitors and Activators of SPP Phosphatase Activity

Inhibitors and activators of hSPP1 can be identified in the $^3$H-dihydrosphingosine-1-phosphate phosphatase assay. Compounds diluted in DMSO, methanol, or other solvent, are added to assays with membranes prepared from cells expressing hSPP1, and dihydrosphingosine-1-phosphate phosphatase activity is measured as in Example 4. Compounds that reduce the $^3$H-dihydrosphingosine recovered in the chloroform layer are inhibitors of phosphatase activity, while compounds that increase $^3$H-dihydrosphingosine are activators. A semi-high throughput dihydrosphingosine-1-phosphate phosphohydrolase assay can be run in tube strips with an assay volume of 100 µl containing 50 mM $KPO^4$ pH 7.2, 0.02% tergitol (NP-40), 2 µM [$^3$H]dihydrosphingosine-1-phosphate (40,000 cpm), 2 mM semicarbazide, and membrane protein prepared from hSPP1 expressing cells. Following a 45 min incubation at 37° C., the assay can be terminated with 100 µl 7 M $NH_4OH$ and 0.5 ml of chloroform:methanol (3:2). Using a robotic pipetting station, 50 µl of the chloroform layer can be distributed into a 96-well T-tray (WALLAC). The T-trays can be air dried, scintillant added, and then counted in a Betaplate scintillation counter (WALLAC).

EXAMPLE 7

Yeast Based Screen for Inhibitors of SPP Phosphatase

Yeast sphingoid base phosphate phosphatase activity is not essential except in combination with other mutations in sphingolipid metabolism. One such lethal combination is lbp1□dpl1□sur2□, which will be dependent on functional expression of hSPP1 for growth and survival. To construct the strain that carries disruptions of the essential combination of 3 yeast genes and expresses hSPP1 for growth, hSPP1 can be subcloned into a yeast expression vector (pRS414-ADH/TRP) and then transformed into a diploid strain lbp1□::LEU2/LBP1, dpl1□::HIS3/dpl1□::HIS3, sur2□::URA3/sur2□::URA3, sporulated, and Trp+, Leu+, His+, Ura+ segregants can be isolated. Inhibitors of hSPP1 phosphatase activity are expected to inhibit the growth of the strain, which can be measured in a 96-well or 384-well spectrophotometric assay.

Compounds diluted in DMSO, methanol, or other solvent, are added to wells and inoculated with logarithmic phase cells incubated in SC-TRP media. After 24 hours incubation at 30° C., the $OD_{600}$ can be measured in a microplate spectrophotometer. Compounds that reduce the $OD_{600}$ compared to solvent treated cells are potential inhibitors. To distinguish specific hSPP1 phosphatase inhibitors from compounds that inhibit yeast growth via other mechanisms, the compounds can be tested for growth inhibition against a wild-type strain, which does not require SPP phosphatase activity for growth, and the compounds can also be screened in an in vitro hSPP1 phosphatase assay as described above.

The Examples have been provided as guidance in practicing the invention and are not limiting of the scope of the invention which is defined by the following claims.

What is claimed:

1. A method of determining whether a candidate compound is an inhibitor of a human sphingosine-1-phosphate phosphatase comprising:
   (a) providing host cells harboring an expression vector that includes a polynucleotide selected from the group consisting of:
      (i) a polynucleotide encoding a polypeptide having the amino acid sequence of SEQ ID NO: 2, and
      (ii) a polynucleotide having the nucleotide sequence of SEQ ID NO: 1,
   (b) contacting said cells with the candidate compound to permit the interaction of the candidate compound with the human sphingosine-1-phosphate phosphatase polypeptide, and
   (c) determining whether the candidate compound is an inhibitor of said human sphingosine-1-phosphate phosphatase polypeptide by ascertaining the activity of the human sphingosine-1-phosphate phosphatase polypeptide in the presence of the candidate compound and comparing said activity to a measurement of the human sphingosine-1-phosphate phosphatase polypeptide activity of the cells before step (b).

2. A method of determining whether a candidate compound is an inhibitor of a human sphingosine-1-phosphate phosphatase polypeptide comprising:
  (a) providing a sample that includes a human sphingosine-1-phosphate phosphatase polypeptide having the amino acid sequence of SEQ ID NO: 2,
  (b) contacting said sample with the candidate compound to permit the interaction of the candidate compound with the human sphingosine-1-phosphate phosphatase polypeptide, and
  (c) determining whether the candidate compound is an inhibitor of said human sphingosine-1-phosphate phosphatase polypeptide by ascertaining the activity of the human sphingosine-1-phosphate phosphatase polypeptide in the presence of the candidate compound and comparing said activity to a measurement of the human sphingosine-1-phosphate phosphatase polypeptide activity of the cells before step (b).

* * * * *

SEQUENCE LISTING

<160> NUMBER OF SEQ ID NOS: 2

<210> SEQ ID NO 1
<211> LENGTH: 1420
<212> TYPE: DNA
<213> ORGANISM: Human

-continued

<400> SEQUENCE: 1

```
cggcccgcct tcccgggggt tccgttatca tgtcgctgag gcagcgcctg gcccagctgg      60
ttggccgtct gcaggacccg cagaaagtgg cccgtttcca gcggctgtgc ggggtggaag     120
cgccgccgcg ccgctcagca gaccggaggg aggatgagaa agcggaggcg cctctcgccg     180
gagaccctcg actgcgaggg cggcagccag ggcgcctgg aggcccccag cctcccggga      240
gcgaccgcaa tcagtgcccg gccaagccgg acggcggcgg cgcccccaac ggcgtgcgga     300
acgggctggc ggccgagctg ggccggcct cgccgcggcg cgcgggcgct ctgcgccgca      360
actcgctgac gggcgaggag ggccagctgg cccgcgtgag caactggccg ctctactgcc     420
tgttctgctt cggcacggag ctgggcaacg aactcttcta catcctgttc ttccccttct     480
ggatctggaa cctggaccct ctggtgggcc ggaggctcgt ggtcatctgg gtgctggtca     540
tgtacctggg ccagtgcacc aaggacatca tccgctggcc gaggcccgcc tcgccgcccg     600
tggtcaagtt ggaggtcttc tacaactctg agtacagcat gccctccacc catgccatgt     660
ccggcaccgc catccccatt tctatggtcc tcctcaccta tggccgctgg cagtaccctc     720
ttatatatgg actgattctt attccctgct ggtgttctct agtttgccta agtagaattt     780
acatgggaat gcactctatt ctggatatta ttgctggatt cctatatacc atttaatct      840
tagctgtctt ctatccattt gtggacctga ttgacaactt caaccaaact cacaaatatg     900
ctccattcat catcatcggg cttcatttag ctttggggat cttttctttc actcttgaca     960
cctggagcac atcccgagga gacacagccg agatactagg aagtggtgct ggaattgcat    1020
gtggatctca tgttacttat aacatgggtc tagtattaga tccttctcta gatacattac    1080
ctttagctgg gccccccatt actgtgactc tgtttggaaa agccatattg cggatcctca    1140
tagggatggt atttgtacta ataatcagag atgtaatgaa aaagatcacc attcctttag    1200
cctgcaaaat cttcaatata ccgtgtgatg atattcgaaa agcaagacag cacatggaag    1260
ttgaacttcc ttatcggtat attacctatg gaatggttgg tttctccatc acatttttg    1320
ttccttacat atttttcttt attggtatct cttgatggag aagtattgtt tatgataaga    1380
aaggagggta tcagttactg ataccccaaaa atatattcca                         1420
```

<210> SEQ ID NO 2
<211> LENGTH: 441
<212> TYPE: PRT
<213> ORGANISM: Human

<400> SEQUENCE: 2

```
Met Ser Leu Arg Gln Arg Leu Ala Gln Leu Val Gly Arg Leu Gln Asp
  1               5                  10                  15

Pro Gln Lys Val Ala Arg Phe Gln Arg Leu Cys Gly Val Glu Ala Pro
             20                  25                  30

Pro Arg Arg Ser Ala Asp Arg Arg Glu Asp Glu Lys Ala Glu Ala Pro
         35                  40                  45

Leu Ala Gly Asp Pro Arg Leu Arg Gly Arg Gln Pro Gly Ala Pro Gly
     50                  55                  60

Gly Pro Gln Pro Pro Gly Ser Asp Arg Asn Gln Cys Pro Ala Lys Pro
 65                  70                  75                  80

Asp Gly Gly Gly Ala Pro Asn Gly Val Arg Asn Gly Leu Ala Ala Glu
                 85                  90                  95

Leu Gly Pro Ala Ser Pro Arg Arg Ala Gly Ala Leu Arg Arg Asn Ser
            100                 105                 110
```

-continued

```
Leu Thr Gly Glu Glu Gly Gln Leu Ala Arg Val Ser Asn Trp Pro Leu
        115                 120                 125
Tyr Cys Leu Phe Cys Phe Gly Thr Glu Leu Gly Asn Glu Leu Phe Tyr
        130                 135                 140
Ile Leu Phe Phe Pro Phe Trp Ile Trp Asn Leu Asp Pro Leu Val Gly
145                 150                 155                 160
Arg Arg Leu Val Val Ile Trp Val Leu Val Met Tyr Leu Gly Gln Cys
                165                 170                 175
Thr Lys Asp Ile Ile Arg Trp Pro Arg Pro Ala Ser Pro Pro Val Val
                180                 185                 190
Lys Leu Glu Val Phe Tyr Asn Ser Glu Tyr Ser Met Pro Ser Thr His
        195                 200                 205
Ala Met Ser Gly Thr Ala Ile Pro Ile Ser Met Val Leu Leu Thr Tyr
        210                 215                 220
Gly Arg Trp Gln Tyr Pro Leu Ile Tyr Gly Leu Ile Leu Ile Pro Cys
225                 230                 235                 240
Trp Cys Ser Leu Val Cys Leu Ser Arg Ile Tyr Met Gly Met His Ser
                245                 250                 255
Ile Leu Asp Ile Ile Ala Gly Phe Leu Tyr Thr Ile Leu Ile Leu Ala
                260                 265                 270
Val Phe Tyr Pro Phe Val Asp Leu Ile Asp Asn Phe Asn Gln Thr His
        275                 280                 285
Lys Tyr Ala Pro Phe Ile Ile Ile Gly Leu His Leu Ala Leu Gly Ile
        290                 295                 300
Phe Ser Phe Thr Leu Asp Thr Trp Ser Thr Ser Arg Gly Asp Thr Ala
305                 310                 315                 320
Glu Ile Leu Gly Ser Gly Ala Gly Ile Ala Cys Gly Ser His Val Thr
                325                 330                 335
Tyr Asn Met Gly Leu Val Leu Asp Pro Ser Leu Asp Thr Leu Pro Leu
                340                 345                 350
Ala Gly Pro Pro Ile Thr Val Thr Leu Phe Gly Lys Ala Ile Leu Arg
        355                 360                 365
Ile Leu Ile Gly Met Val Phe Val Leu Ile Ile Arg Asp Val Met Lys
        370                 375                 380
Lys Ile Thr Ile Pro Leu Ala Cys Lys Ile Phe Asn Ile Pro Cys Asp
385                 390                 395                 400
Asp Ile Arg Lys Ala Arg Gln His Met Glu Val Glu Leu Pro Tyr Arg
                405                 410                 415
Tyr Ile Thr Tyr Gly Met Val Gly Phe Ser Ile Thr Phe Phe Val Pro
                420                 425                 430
Tyr Ile Phe Phe Phe Ile Gly Ile Ser
        435                 440
```